United States Patent [19]

Pettersson

[11] 4,110,331

[45] Aug. 29, 1978

[54] METHOD OF PRODUCING THE HYDROCHLORIDE OF N-METHYL PIPERIDINE-2-CARBOXYLIC ACID-2,6-XYLIDIDE

[75] Inventor: Bror Gösta Pettersson, Karlskoga, Sweden

[73] Assignee: AB Bofors, Bofors, Sweden

[21] Appl. No.: 806,632

[22] Filed: Jun. 15, 1977

[30] Foreign Application Priority Data

Jun. 22, 1976 [SE] Sweden ............................ 7607114

[51] Int. Cl.² ................ C07D 211/60; C07D 211/02
[52] U.S. Cl. .............................................. 260/293.77
[58] Field of Search ................................... 260/293.77

[56] References Cited

FOREIGN PATENT DOCUMENTS 2,259,517   6/1973   Fed. Rep. of Germany.
772,807   4/1957   United Kingdom.
824,542   12/1959   United Kingdom.
869,978   6/1961   United Kingdom.
1,110,637   4/1968   United Kingdom .................. 546/239

Primary Examiner—Norma S. Milestone
Attorney, Agent, or Firm—Pollock, Vande Sande & Priddy

[57] ABSTRACT

Method for producing the hydrochloride of N-methyl piperidine-2-carboxylic acid-2,6-xylidide which include hydrogenating picolinic acid-2,6-xylidide in the pyridine ring in the presence of HCl to the hydrochloride of piperidine carboxylic acid xylidide followed by catalytic reductive methylation using formaldehyde.

18 Claims, No Drawings

METHOD OF PRODUCING THE HYDROCHLORIDE OF N-METHYL PIPERIDINE-2-CARBOXYLIC ACID-2,6-XYLIDIDE

The present invention relates to a method, starting with picolinic acid-2,6-xylidide according to the formula

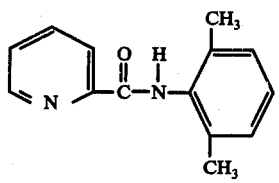

of producing N-methyl piperidine-2-carboxylic acid-2,6-xylidide according to the formula

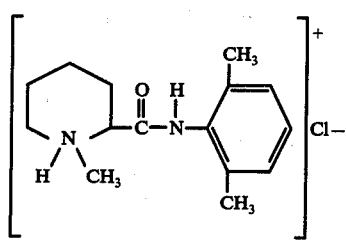

The characteristics of the invention will be noted from the accompanying claims.

According to the Swedish Pat. Nos. 164 063 and 189 097, N-methyl piperidine-2-carboxylic acid-2,6-xylidide is known as a local anaesthetic. In previously used production methods, it has been necessary to use chemicals which are unsuitable from the point of view of pollution, such as the toxic methylation agent dimethyl sulphate. Through the present invention, the dimethyl sulphate is replaced by the less dangerous formaldehyde. The methylation with the formaldehyde is a catalytic reductive methylation conducted under superatmospheric pressure in a hydrogen atmosphere. It is believed that the hydrogen acts as a reductive catalyst. The applied hydrogen pressure may be between 5 and 15 atmospheres, preferably 10 atmospheres. Further, the production can take place without isolation of intermediates, and this involves a more simple process and, moreover, gives a higher yield. It is essential in this connection that the least possible quantity of water is present at the reaction, and the formaldehyde used can therefore appropriately be added in the form of paraformaldehyde. However, it is also possible to use formalin, but this gives lower yields. The water which is added, and that which is formed during the reaction, can appropriately be removed by means of azeotropic distillation, in which e.g. toluene or ethanol is used as an entrainer. Ethanol or methanol can appropriately be used as a solvent for the reaction. The invention will now be described in more detail, which reference to the following examples of the procedure.

EXAMPLE 1

Charge 68 parts by weight picolinic acid-2,6-xylidide into an autoclave with stirrer, together with 275 parts by weight 99% ethanol and 31 parts by weight 36% hydrochloric acid. As a catalyst, use 1 part by weight carbon containing 3% platinum. The hydrogenation should be carried out at 10 atmospheres hydrogen gas pressure and a temperature of 90°–100° C., and after a reaction time of about 2 hours, this hydrogenation has been completed. Without filtering off the hydrogenation catalyst used (platinum on carbon) add 3 parts by weight of a methylation catalyst consisting of carbon with 5% palladium, which catalyst should be suspended in 40 parts by weight ethanol Further to this, add 10 parts by weight paraformaldehyde, and a methylation takes place at 10 atmospheres hydrogen gas pressure and a temperature of 100°–100° C. After 5–6 hours reaction time, the methylation has been completed.

When the reaction mixture has been allowed to cool to approx. 70° C., filter off the catalysts and add 110 parts by weight toluene. The mixture should thereafter be subjected to azeotropic distillation, and when 300–350 parts by weight have been distilled off, approx. 6% water (counted on the ethanol charged) has been removed.

After the azeotropic distillation, the ethanol solution should be cooled to approx. 0° C., for crystallization of the product desired, the hydrochloride of N-methyl piperidine-2-carboxylic acid-2,6-xylidide. This should be filtered off and thereafter washed with acetone, and dried at 100° C. The yield is 78 parts by weight or 92% counted on the picolinic acid xylidide used. The product is obtained in a very pure form, with a melting point of 262°–64° C.

Alternatively, the hydrogenation catalyst can be filtered off before the methylation catalyst is added, but this does not noticeably affect either the yield or the purity of the product obtained.

EXAMPLE 2

Hydrogenation and methylation takes place in the same way as described in Example 1, but instead of distilling off the water by means of azeotropic distillation, after cooling, neutralize the reaction mixture with sodium hydroxide to pH 11. After further cooling, filter off the N-methyl piperidine-2-carboxylic acid-2,6-xylidide formed, which after washing with water should be dried in vacuum at 50° C. The yield is then 65 parts by weight or 88% counted on the picolinic acid xylidide used. The base obtained has good purity and a melting point of 150°–52° C.

In order to obtain the hydrochloride desired, dissolve one part by weight of the base in 4 parts by weight 99% ethanol, and in this ethanol solution thereafter introduce hydrochloric acid gas to pH 4. After cooling of the reaction mixture, filter off the crystallized product, which should thereafter be washed with ethanol, followed by drying at 100° C. The hydrochloride of the N-methyl piperidine-2-carboxylic acid-2,6-xylidide obtained has good purity and a melting point of 262°–64° C.

EXAMPLE 3

The hydrogenation takes place as described in Example 1, but the hydrogenation product should be isolated from the ethanol solution through cooling, and the hydrochloride of the piperidine-2-carboxylic acid-2,6-xylidide will then crystallize. The yield is 95% counted on the picolinic acid xylidide used, and the melting point of the product is 264°–65° C.

The hydrogenation product obtained should be methylated in the same way, in principle, as described in Example 1, but with the difference that to 80 parts by weight of the hydrochloride of the piperidine-2-carboxylic acid-2,6-xylidide should be added 27 parts by weight 35% formalin. After azeotropic distillation as described above, using toluene, approx. 6% water has been distilled off, and 76 parts by weight hydrochloride of N-methyl piperidine-2-carboxylic acid-2,6-xylidide will crystallize. The yield is then 90%, and the melting point of the product is 262°-64° C.

EXAMPLE 4

Also in this case, hydrogenation and methylation should take place in the same way as described in Example 1. However, one different is that the paraformaldehyde is replaced by 27 parts by weight 37% formalin. In this case, approx. 10% water can be distilled off through the azeotropic distillation.

From the ethanol solution obtained after the azeotropic distillation, through cooling to 0° C. a crystallized product is obtained which is filtered off and washed with acetone in the way described in Example 1. In this case, the hydrochloride of the N-methyl piperidine-2-carboxylic acid-2,6-xylidide is obtained in a yield of 54% or 46 parts by weight. Through further distillation of the ethanol from the mother liquid, a second fraction of crystallized product is obtained. The yield is then approx. 27% or 23 parts by weight, and the total yield obtained is therefore 69 parts by weight or 81%. The product should be dried at 100° C., and has a melting point of 262°-64° C.

EXAMPLE 5

The production is carried out in the same way as described in Example 1, but for the azeotropic distillation, ethanol is used instead of toluene as an entrainer.

After the catalysts have been filtered off, add 150 parts by weight 99% ethanol, and when 300 parts by weight ethanol have been distilled off and have then taken along approx. 5% water through the azeotropic distillation, cool the ethanol solution. After filtering, washing with acetone and drying at 100° C., 78 parts by weight of the hydrochloride of N-methyl piperidine-2-carboxylic acid-2,6-xylidide will be obtained. This corresponds to a yield of 92% counted on the picolinic acid xylidide used, and the product obtained has good purity and a melting point of 262°-64° C.

I claim:

1. A method of producing the hydrochloride of N-methyl piperidine-2-carboxylic acid-2,6-xylidide of the formula:

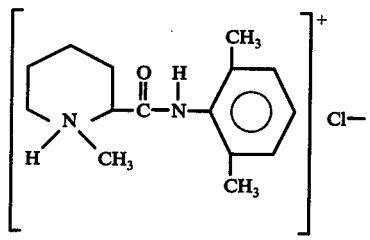

which comprises hydrogenating picolinic acid-2,6-xylidide of the formula:

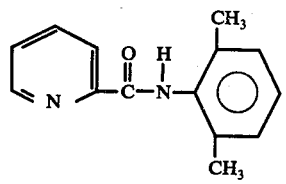

in the pyridine ring in the presence of hydrochloric acid to provide the hydrochloride of piperidine carboxylic acid xylidide which thereafter using formaldehyde is subjected to catalytic reductive methylation.

2. A method according to claim 1, characterized in that the formaldehyde is used in the form of paraformaldehyde.

3. A method according to claim 1, characterized in that the formaldehyde is used in the form of formalin.

4. A method according to claim 1, characterized in that the water is removed from the reaction mixture by means of azeotropic distillation.

5. A method according to claim 4, characterized in that the azeotropic distillation is carried out with the aid of toluene.

6. A method according to claim 4, characterized in that the azeotropic distillation is carried out with the aid of ethanol.

7. A method according to claim 1, characterized in that the hydrogenation and methylation is carried out in one step, without isolation of intermediates.

8. A method according to claim 1, characterized in that the hydrogenation and methylation is carried out in an ethanol solution.

9. A method according to claim 8, characterized in that 1 equivalent hydrochloric acid has been added to the ethanol solution.

10. A method according to claim 1, characterized in that the methylation is carried out at a temperature of between 75° and 120° C.

11. The method of claim 1 wherein said methylation is conducted under superatmospheric pressure in a hydrogen atmosphere.

12. The method of claim 11 wherein the pressure of the hydrogen is between 5 and 15 atmospheres.

13. The method of claim 1 wherein the hydrogenation is carried out in the presence of a 3% platinum on carbon catalyst.

14. The method of claim 1 wherein the methylation is carried out in the presence of a 5% palladium on carbon catalyst.

15. The method of claim 1 wherein said formaldehyde is used in the form of paraformaldehyde, water is removed from the reaction mixture by means of azeotropic distillation, the hydrogenation and methylation are carried out in an ethanol solution and in one step without isolation of intermediates, said ethanol solution contains one equivalent hydrochloric acid, wherein the methylation is carried out at a temperature of between 75 and 120° C. under superatmospheric pressure in a hydrogen atmosphere at hydrogen pressure of between 5 and 15 atmospheres.

16. The method of claim 15 wherein the hydrogenation is carried out in the presence of a 3% platinum on carbon catalyst.

17. The method of claim 15 wherein the methylation is carried out in the presence of a 5% palladium on carbon catalyst.

18. The method of claim 16 wherein the catalyst used in the hydrogenation is not removed from the reaction mixture prior to the methylation.